(12) United States Patent
Freud et al.

(10) Patent No.: US 9,802,061 B2
(45) Date of Patent: Oct. 31, 2017

(54) APPARATUS FOR PARTICLE THERAPY VERIFICATION COMPRISING A COLLIMATOR WITH MULTIPLE OPENINGS

(71) Applicants: ION BEAM APPLICATIONS S.A., Louvain-la-Neuve (BE); Université Claude Bernard Lyon 1, Villeurbanne (FR); Institut National des Science Appliquées de Lyon, Villeurbanne (FR); Centre National de Recherche Scientifique (CNRS)

(72) Inventors: Nicolas Freud, Lyons (FR); Frauke Roellinghoff, Frankfurt (DE); Etienne Testa, Lyons (FR); Marco Pinto, Lyons (FR); Julien Smeets, Bouge (BE)

(73) Assignees: Ion Beam Applications S.A., Louvain-la-Neuve (BE); Université Claude Bernard Lyon 1, Villeurbanne (FR); Institut National des Science Appliquées de Lyon, Villeurbanne (FR); Centre National de Recherche Scientifique (CNRS), Paris (FR)

( * ) Notice: Subject to any disclaimer, the term of this patent is extended or adjusted under 35 U.S.C. 154(b) by 0 days.

(21) Appl. No.: 14/707,828

(22) Filed: May 8, 2015

(65) Prior Publication Data

US 2015/0321025 A1    Nov. 12, 2015

(30) Foreign Application Priority Data

May 9, 2014   (EP) .................................... 14167652

(51) Int. Cl.
*A61N 5/10* (2006.01)
*A61B 6/00* (2006.01)
*G01T 1/29* (2006.01)

(52) U.S. Cl.
CPC .......... *A61N 5/1071* (2013.01); *A61B 6/4216* (2013.01); *A61B 6/4258* (2013.01);
(Continued)

(58) Field of Classification Search
CPC .............................. G01T 1/026; A61N 5/1071
See application file for complete search history.

(56) References Cited

U.S. PATENT DOCUMENTS

2011/0057110 A1*   3/2011   Testa et al. .............. 250/370.07
2011/0186720 A1*   8/2011   Jongen et al. ............. 250/252.1
2014/0061493 A1*   3/2014   Prieels et al. ................. 250/393

FOREIGN PATENT DOCUMENTS

WO   WO 2009/141570    11/2009
WO   WO 2012/104416    8/2012

OTHER PUBLICATIONS

Chul Hee Min et al., Development of array-type prompt gamma measurement system for in vivo range verification in proton therapy, 2100 Med. Phys. 39(4), Apr. 2012, pp. 2100-2107 (8 pgs).

(Continued)

*Primary Examiner* — David Porta
*Assistant Examiner* — Hugh H Maupin
(74) *Attorney, Agent, or Firm* — Finnegan, Henderson, Farabow, Garrett & Dunner LLP (57) ABSTRACT

The disclosure is related to an apparatus and method for charged hadron therapy verification. The apparatus comprises a collimator comprising a plurality of collimator slabs of a given thickness, spaced apart so as to form an array of mutually slit-shaped openings, configured to be placed at a right angle to the beam line, so as to allow the passage of prompt gammas from the target, the collimator being defined at least by three geometrical parameters being the width and depth of the slit-shaped openings and a fill factor. The (Continued)

disclosure is also related to a method for charged hadron therapy verification with a multi-slit camera.

20 Claims, 2 Drawing Sheets

(52) U.S. Cl.
CPC .......... *A61B 6/4291* (2013.01); *A61N 5/1031* (2013.01); *A61N 5/1075* (2013.01); *G01T 1/29* (2013.01); *A61N 5/1043* (2013.01); *A61N 2005/1034* (2013.01); *A61N 2005/1076* (2013.01); *A61N 2005/1087* (2013.01)

(56) References Cited

OTHER PUBLICATIONS

J. Smeets etc., Prompt gamma imaging with a slit camera for real-time range control in proton therapy, Phys. Med. Biol. 57 (2012) 3371-3405. (35 pgs).
Chul Hee Min et al., Prompt gamma measurements for locating the dose falloff region in the proton therapy, Applied Physics Letters 89, 183517-183517-3 (2006). (3 pgs).

* cited by examiner

APPARATUS FOR PARTICLE THERAPY VERIFICATION COMPRISING A COLLIMATOR WITH MULTIPLE OPENINGS

CROSS-REFERENCE TO RELATED APPLICATIONS

This U.S. patent application claims priority under 35 U.S.C. §119 to: European Patent Application No. EP14167652, filed May 9, 2014. The aforementioned application is incorporated herein by reference in its entirety.

TECHNICAL FIELD

The disclosure is related to the field of charged Hadron Therapy, i.e. radiation therapy using particles, such as protons or ions (e.g. carbon ions). More particularly, the disclosure is related to a detection system for measuring the beam range of a charged hadron beam in a target object.

BACKGROUND

Charged hadrons (i.e. protons, pions, ions such as carbon ions) have physical advantages with respect to X-rays or gamma rays in the field of radiation therapy. For example, protons of a given energy (i.e. forming a mono-energetic proton beam), have a certain penetration depth in a target object and do not penetrate beyond that depth, and furthermore, they deposit their maximum amount of energy or dose in the so-called Bragg Peak, which corresponds to said penetration depth, i.e. the point of greatest penetration of the radiation in the target volume. The position of the Bragg peak is also related to the 'beam range', which is usually defined as the position where the dose is 80% of the value at the Bragg peak. Since the Bragg peak position depends on the energy of the hadron beam, it is evident that by precisely controlling and modifying the energy, one can place the Bragg Peak at a given depth of a tumour so as to administer the greatest radiation energy to selected points and spare the healthy tissue surrounding said points.

As a consequence, the location of the Bragg peak must be precisely known since critical tissue localized near the target tumour could receive an excessive dose, whereas conversely the target tumour could receive an insufficient dose. There is a need therefore to obtain a direct on-line, i.e. during beam delivery, measurement of the particle range.

One option which has been explored is the detection of prompt gammas emitted from a target irradiated by a charged hadron beam. Prompt gammas are emitted isotropically from every location along the charged hadron beam path in the target, so that this path is seen as a gamma line source by a detection apparatus. The detection of said prompt gammas offers a possibility of determining the beam range. One solution of this type is disclosed in the document 'Prompt gamma measurements for locating the dose falloff region in the proton therapy', Chul-Hee Min and Chan Hyeong Kim, 2006 Applied Physics Letters, article 183517. The authors used a gamma scintillation camera equipped with one multilayered collimator system to measure prompt gamma generated by irradiation. Nevertheless, this device is only able to detect prompt gamma emitted from 90° of the beam direction. To obtain the prompt gamma distribution along the beam direction, the detector may be moved step by step to different measurement positions which makes this device not useful for practical on-line measurements.

In the document 'Development of an array-type prompt gamma detection system for in vivo range verification in proton therapy', Chul-Hee Min et al, Med. Phys. 39(4), April 2012, pp 2100-2107, a linear array of scintillation detectors and photodiodes is disclosed for the online measurement of the proton beam range. This study discloses a collimator with a plurality of slits, for detection of the beam range in a target. The optimal dimensions of the slits and collimation depths disclosed in this document are as follows: slit width 2 mm, septum width 2 mm, collimator depth 150 mm, pitch 4 mm. These dimensions however do not allow sufficiently high statistics of the detected prompt gammas, as will be explained in the detailed description of the present disclosure.

Further previous studies have explored the possibility of verifying the beam range in a target by detecting shifts of a prompt gamma profile with respect to a reference profile. This approach has been described for the case of a so-called 'knife-edge' slit prompt gamma camera in document WO2012104416 and in 'Prompt gamma imaging with a slit camera for real-time range control in proton therapy', Smeets et al, Physics in Medicine and Biology, 57(11), 3371-3405.

SUMMARY

The disclosure is related to an apparatus and method as disclosed in the appended claims. The disclosure is firstly related to an apparatus for charged hadron therapy verification by detecting prompt gammas produced when irradiating a target with a charged hadron beam, the beam being directed along a beam line, said apparatus comprising:
  a collimator comprising a plurality of collimator slabs of thickness t, spaced apart so as to form an array of slit-shaped openings, configured to be placed at a right angle to the beam line, so as to allow the passage of prompt gamma emission from the target, the collimator being defined at least by three geometrical parameters being: the width (s) and depth (D) of the slit-shaped openings and the fill factor (f), with f equal to t/(t+s),
  a detection device suitable for detecting said prompt gamma emission, comprising at least a portion of scintillator material aligned with each of said slit-shaped openings,
characterized in that the width s of the openings, the depth D of the openings and the fill factor f are chosen such that:
  s is 3 mm or higher
  D is between 50 mm and 200 mm
  f is lower than 0.5.

According to a preferred embodiment, the detection device is configured to determine a profile of prompt gammas detected through the slit-shaped openings and the apparatus comprises computer means configured for comparing said profile of prompt gammas with a reference profile so as to determine a shift of a penetration depth of the hadron beam.

According to an embodiment, the detection device is configured to determine a profile of prompt gamma count values as a function of the position along the beam line, and wherein the apparatus comprises a means for determining a shift of the profile with respect to a reference profile, in the direction of the beam line.

According to a further embodiment, the detection device comprises:
  detectors in connection with said portions of scintillating material, for producing a signal related to the number of photon counts registered in said portions of scintillating material, and a processor for receiving and processing said signals to thereby determine said profile, hereafter referred to as the newly acquired profile, wherein the processor is further configured to receive a reference profile, and determine the shift in the direction of the beam line, of the newly acquired profile with respect to the reference profile.

According to a preferred embodiment, the collimator material is tungsten.

According to an embodiment, D is between 50 mm and 100 mm. According to other embodiments, s is between 3 mm and 12 mm or s is larger than 4 mm. According to an embodiment, f is at least 0.25.

According to an embodiment, the pitch p, with p=t+s, of said array of openings is equal to 5 mm or higher. According to a further embodiment, the pitch p is between 5 mm and 20 mm.

According to an embodiment, the openings as well as the slabs have mutually parallel sidewalls.

The disclosure is also related to a method for charged hadron therapy verification by detecting prompt gammas produced when irradiating a target with a charged hadron beam, the beam being directed along a beam line, wherein the prompt gammas are detected with an apparatus comprising:
  a collimator comprising a plurality of collimator slabs of thickness t, spaced apart so as to form an array of slit-shaped openings, placed at an essentially right angle to the beam line, so as to allow the passage of prompt gamma emission from the target, the collimator being defined at least by three geometrical parameters being: the width (s) and depth (D) of the slit-shaped openings and the fill factor (f), with f equal to t/(t+s),
  a detection device suitable for detecting said prompt gammas emission, comprising at least a portion of scintillator material aligned with each of said slit-shaped openings,
wherein the width s of the openings, the depth D of the openings and the fill factor f are chosen such that:
s is 2 mm or higher
D is between 50 mm and 200 mm
f is lower than or equal to 0.7
a Time of Flight (TOF) discrimination may be applied to the detection of the prompt gammas, and wherein J>1%, with J defined as $$\frac{S \cdot A}{\sqrt{A_{TOF}}}$$

wherein:
S=spatial acceptance=$1-f=s/(s+t)$
A=angular acceptance=slit width/collimator depth (s/D)
$A_{TOF}$=TOF acceptance=the ratio of neutron background emission that is conserved after application of the TOF discrimination, to the total neutron background emission, with $A_{TOF}=1$ when no TOF discrimination is applied.

The method preferably comprises the steps of determining a profile of prompt gamma count values as a function of the position along the beam line, and of determining the shift of the profile with respect to a reference profile. Said profile is preferably expressed as the number of counts per hadron and per unit distance, as a function of said position along the beam line.

According to an embodiment of the method, s is 3 mm or higher and f is lower than 0.5. According to another embodiment, a TOF discrimination is applied, i.e. wherein $A_{TOF}$ is lower than 1.

According to an embodiment of the method of the disclosure, the target is a water phantom. According to further embodiments, value of J answers to the following conditions respectively: J>1.5%, J>2%, J>2.5%, J>3%.

According to a preferred embodiment, the method comprises the steps of determining a profile of prompt gamma count values as a function of the position along the beam line, and of determining the shift of the profile with respect to a reference profile.

According to a further embodiment, the method comprises the steps of:
  acquiring a new profile of prompt gamma count values as a function of the position along the beam line, the prompt gammas being emitted from a target that is being irradiated by a hadron beam directed along a beam line,
  acquiring a reference profile, which may be a profile obtained from simulated data or from a previous measurement,
  determining the shift of new profile with respect to the reference profile, in the direction of the beam line.

DETAILED DESCRIPTION

Figure 1:
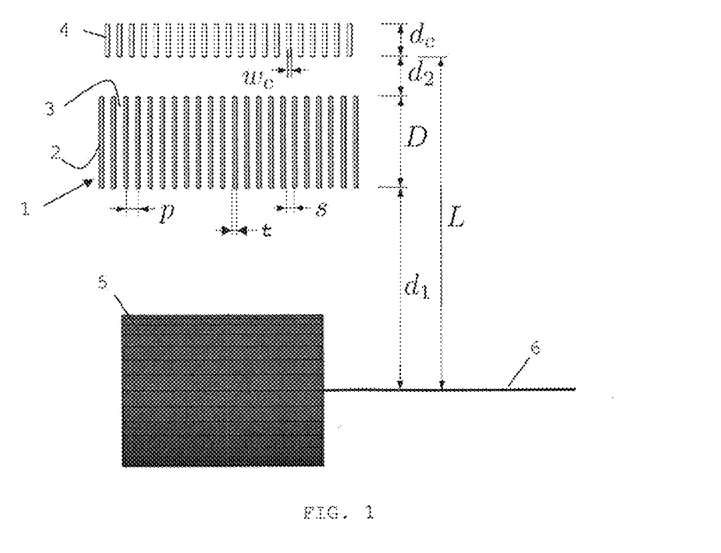
FIG. 1 shows the geometry of a multi-slit prompt gamma camera set-up.

FIG. 1 illustrates the geometry of a multi-slit prompt gamma verification apparatus according to one embodiment of the disclosure. Hereafter the apparatus will be referred to as a 'prompt gamma camera'. The apparatus comprises a collimator 1 comprising a series of slabs 2 of shielding material, spaced apart at equal distances, to form an array of slit-shaped openings 3. The distance between two adjacent slabs 2 defines the width s of the openings 3. The thickness of the slabs is called the septum t. As all the openings and collimator slabs have the same width and thickness respectively, the pitch p is the sum of one value of the septum and the slit width (p=t+s). The fill factor f is equal to t/p and gives an idea of the relative importance of the slab material in the array. The slit width s can be expressed as p(1−f). Inversely, the fill factor f equals (p−s)/p. The width s and septum t are preferably constant as in the case of the embodiment of FIG. 1, i.e. the collimator slabs have two mutually parallel side walls and are placed parallel to each other in the array of collimator slabs. However, the disclosure does not exclude embodiments wherein the width s and/or the septum t are not constant, because s and t differ for at least some of openings/slabs in the array and/or because one or more openings or slabs do not have parallel sidewalls. When s and/or t are not constant, all statements made in the present description and in the appended claims regarding values of these parameters s and t are related to the average value of s and t, the average being calculated for each opening and each slab, and then averaged out over all the openings and slabs of the array.

The camera is mounted with respect to a target 5 that is irradiated by a hadron beam directed along a beam line 6, in such a way that the slit-shaped openings 3 are essentially perpendicular to the beam line 6. The beam line or beam axis 6 is defined as the direction of the hadron beam when the beam is not deflected in the direction perpendicular to said beam line. When a beam is scanned over a target, such deflection takes place by deflection magnets. Therefore, within the context of this description the wording 'a hadron beam directed along a beam line' may be understood as 'a hadron beam having the direction of a beam line or being deflected with respect to said beam line in the direction perpendicular to said beam line'. For the sake of conciseness, the former expression is used in the description and claims.

The apparatus or camera according to the disclosure comprises a detection device configured to determine a profile of prompt gammas detected through the slit-shaped openings. As the slit-shaped openings are essentially perpendicular to the beam line, the determined profile is expressing a number of prompt gamma counts as function of a position along a beam line direction.

A preferred embodiment of the disclosure comprises computer means configured for comparing the profile of the measured prompt gammas with a reference profile so as to determine a shift of a penetration depth of the hadron beam. The computer means can for example be a computer configured with computer algorithms to compare the prompt gamma profile with the reference profile. Those algorithms for comparing two profiles are known in the art, for example curve matching algorithms or alternatively curve fitting methods can be used. The computer means are further configured to determine a shift of a penetration depth of the hadron beam based on the comparison of the prompt gamma profile with the reference profile. Indeed, it is well known in the art that the prompt gamma profiles are associated with the Bragg peak distribution and hence an observed shift of a prompt gamma profile can be associated with a shift in the penetration depth of the hadron beam. The reference prompt gamma profile may be obtained through a Monte Carlo simulation or through an analytical model calculation or obtained through a previous measurement.

The camera comprises a detection device suitable for detecting the prompt gamma emission. The detection device comprises an array of slabs 4 of scintillator material, each scintillator slab having a width $w_c$ that is aligned with one opening 3. The width $w_c$ of the scintillator slabs may be equal to the width s of the openings 3. The width $w_c$ may equally be smaller or larger than said opening width s. Alternatively, a solid block of scintillating material may be used instead of the array of separate scintillator slabs 4. The detection device further comprises, in connection with the scintillator slabs 4, detectors such as photomultiplier tubes (not shown in the drawing), for detecting light emitted by the scintillator slabs as a consequence of radiation particles incident on the scintillator material, in practice mainly neutrons and photons. The detection device further comprises a processor for receiving a signal from the detectors and calculating from said signals the number of photon counts as a function of the position along the beam line, i.e. a profile of detected radiation emitted from positions within the target, in the direction of the beam line. The processor is equally configured to derive from said number of photon counts the dose delivered to the target as a function of said position along the beam line.

The entrance to the collimator openings 3 is located at a distance $d_1$ from the beam line 6. The depth D of the collimator openings 3 is the width of the slabs 2 measured from the entrance of the openings, i.e. in the direction perpendicular to the beam line 6 when the camera is mounted with the openings perpendicular to the beam. The dimensions $d_c$, $d_2$ and L are self-explanatory. The collimator slabs 2 are preferably rectangular shaped, extending along a given height perpendicular to the plane of the drawing in FIG. 1. The height of the scintillator slabs 4 is preferably the same as the height of the collimator slabs 2. The apparatus is mounted in a housing (not shown), possibly separate housings for the collimator 1 and the scintillator slabs 4. The details of how the incident radiation is detected and measured via the scintillator slabs and detectors, and subsequently processed to obtain a profile of detected radiation along the beam line are not explained here, as these are considered known to a person skilled in the art.

With the help of simulations described in more detail at a later stage of this description, the inventors of the present disclosure have optimized the dimensions of the camera configuration of FIG. 1 with the aim of obtaining a prompt gamma profile that allows detection of a shift of the profile (in case of range shift or target shift) with a precision that is better when compared to similar prompt gamma camera configurations known in the art. A detailed comparison was made between the system described in the above-cited reference by Chul-Hee Min et al from 2012, hereafter referred to as reference 1, and the optimized design. Surprisingly, the inventors have found that a number of the optimized parameters differed in an important way from the parameters of reference 1 (and also differs from intuitively expected values as explained later). The inventors have furthermore determined the conditions under which the improved efficiency referred to above can be achieved, even for multi-slit cameras known in the art, such as the configuration of reference 1.

The ranges for a number of dimensional parameters of the camera according to the disclosure are as follows:

slit width s: 3 mm or higher. The maximum applicable slit opening may be case dependent (for example depending on the intensity of the proton beam, the density of the collimator material and of the crystal material, the details of the treatment case which may use a specific spatial resolution), and can be determined easily by the skilled person. According to an embodiment, the slit width is between 3 and 12 mm. According to a further embodiment, the slit width is larger than 4 mm, for example higher than 4 mm and lower than 12 mm. According to an embodiment, s is 5 mm or higher, for example between 5 mm and 12 mm.

collimator depth D: between 50 and 200 mm, preferably between 50 mm and 100 mm, more preferably equal to or higher than 50 mm and lower than 100 mm. According to further embodiments, the collimator depth is between 50 and 90 mm or between 50 and 80 mm.

fill factor f: lower than 0.5, and higher than a value beneath which insufficient shielding would be available between neighbouring openings 3. The minimum may depend on the collimator material as may be appreciated by the skilled person. According to an embodiment, f is at least 0.25. According to further embodiments, f is between 0.25 and 0.4 or between 0.3 and 0.4.

According to a preferred embodiment, in combination with the above given ranges for s, D and f, the pitch p is minimum 5 mm. According to a further embodiment, the pitch is between 5 mm and 20 mm. The material of the collimator may be lead or any other suitable material. According to a preferred embodiment, the collimator material is tungsten.

With respect to the optimized values of reference 1 mentioned above, namely s=2 mm, D=150 mm and f=0.5 (p=4 mm), the camera of the disclosure distinguishes itself mainly by the fact that the slit width s is higher and the fill factor f is lower. Especially the latter point represents a main distinction compared to the prior art: in a collimator of the disclosure, the width s of the openings is larger than the septum t, i.e. the camera is more 'open'. It is to be noted also that very low values of the depth D of the collimator openings are allowed in a camera of the disclosure compared to the prior art. As will be explained further in this description, the lower values of D (e.g. lower than 100 mm) are actually favoured when the camera is used for prompt gamma detection without so-called Time of Flight (TOF) correction.

The parameter ranges for s, D and f (and p) in a multi-slit camera according to the disclosure have been reached as a consequence of the inventors' approach in simulations performed with the setup of FIG. 1. A Monte Carlo simulation of the camera system of FIG. 1 was performed for modelling the prompt gamma distribution measured by the camera, based on a pencil beam irradiation with a proton beam, with the target 5 being a cylindrical water phantom.

Figure 2:
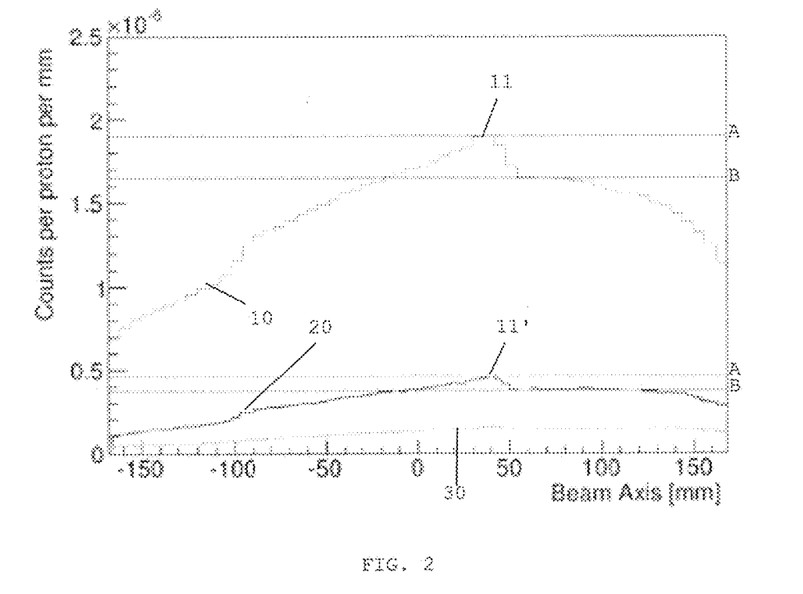
FIG. 2 illustrates prompt gamma profiles obtained from simulations based on a geometry of a prompt gamma camera according the disclosure, and compared to a geometry as known in the art.

The inventors have calculated the actual number of incident counts on the scintillator crystals, for each proton in a typical pencil beam spot irradiation. Each spot is irradiated by a bundle of protons at 160 MeV. The time structure of the proton beam is characterised by beam pulses of width 1 ns with a time delay of 10 ns between pulses (i.e. the time structure of a proton beam produced by a cyclotron with RF accelerator operating at 100 MHz). The number of protons in each bundle is typically between 1E6 and 1E9. The prompt gamma detection profile expressed as the number of counts per proton and per mm along the beam line is depicted in FIG. 2 as profile 10 for the following geometry according to the disclosure:

Geometry 1 depth D of the collimator openings=70 mm, slit width s=3.9 mm, fill factor f=0.35, pitch p=6 mm, beam-collimator distance $d_1$=200 mm, collimator-crystal distance 0 mm, scintillator slab width $w_c$=3.9 mm, scintillator slab height 200 mm, scintillator depth 50 mm. The collimator material taken into account in the simulation was tungsten, the scintillator material LYSO. The energy window selected in the simulations on which profile 10 is based was 2-7 MeV (i.e. only prompt gamma emission and background entering the camera and generating in the crystal an energy that is in that window is taken into account). No Time of Flight window was applied.

Profile 10 exhibits a peak 11 which is correlated to the position of the Bragg peak in the target. The particles emitted from the target that have been taken into account for the simulation are:
  prompt gamma (i.e. photons) that are correlated with the beam range in the target, and
  background emission consisting mainly of neutrons emitted by nuclear reactions along the beam path, which are not correlated with the beam range.

Both types of particles lead to counts registered in the scintillator slabs 4. The values indicated by curve 10 therefore consist of a number of uncorrelated counts and a number of correlated counts. At the peak 11, level A indicates the total number of counts and level B indicates the uncorrelated number of counts. The difference between levels A and B is the number of correlated counts. The following approximate numerical data recorded at the peak position 11 can be derived from profile 10:
  number of correlated counts per proton and per mm (level A-level B): 2.7E-7
  number of uncorrelated counts per proton and per mm (level B): 1.63E-6

The same calculation was done but with the dimensions D, s, p and f according to the preferred dimensions disclosed in reference 1. This calculation was thus based on the following geometry:

Geometry 2 collimator depth D=150 mm, slit width s=2 mm, fill factor f=0.5, pitch p=4 mm, scintillator slab width $w_c$=2 mm. All other parameters and materials as in Geometry 1.

The curve 20 shows the profile of geometry 2 for the energy window 2-7 MeV, i.e. the same window as applied for the simulation of geometry 1, and without applying a TOF window. This allows to compare both geometries in the best possible way.

The following approximate numerical data recorded at the peak position 11' can be derived from profile 20:
  number of correlated counts per proton and per mm (level A-level B): 0.8E-7
  number of uncorrelated counts per proton and per mm (level B): 3.8E-7

Profile 30 shows the profile for geometry 2 for the window 4-10 MeV that was used in the simulation described in reference 1 itself. Also no TOF window was applied in obtaining profile 30.

The spatial resolution of these profiles is evaluated as the FWHM (Full-width-Half-Maximum) of the Gaussian pattern observed in the detection profile when the acquisition of a point source located on the beam axis and emitting gammas at 4.44 MeV is simulated (the intense prompt-gamma ray with a central position in the emission spectrum). This FWHM is thus the size with which a point source is seen on the camera. This spatial resolution has a value of 14 mm for profile 10 obtained with geometry 1. This means that, in practice, two point sources cannot be reliably distinguished unless they are separated by more than 14 mm distance. Geometry 2 achieves better spatial resolution, between 8 and 10 mm depending on the energy selection window, which is a priori expected to result in a better capability to accurately distinguish the penetration depth of the beam from the detection profile. One would a priori not expect a camera with a resolution of 14 mm to be able to distinguish shifts of the penetration depth of the proton beam as small as 1 mm. This is nevertheless possible with a geometry according to the disclosure, as will be presently explained.

From the data derived from profile 20 (geometry 2) we can calculate that for a normal amount of protons of 1E8 in a pencil beam spot, we would obtain about 8 correlated counts (1E8×0.8E-7). For the same spot containing 1E8 protons, the number of uncorrelated counts would be about 38. The natural statistical variation on this number follows a Poisson law: for 38 counts per mm per proton, the statistical uncertainty corresponding to the Poisson law has a standard deviation equal the square root of 38 counts, i.e. about 6 counts, and thus of the same order of magnitude than the number of correlated counts, 8. For lower numbers of protons delivered to a spot, the uncertainty on the number of uncorrelated counts will exceed the number of correlated counts. For most applicable pencil beams therefore, the geometry (geometry 2) of the prior art design is not capable of measuring the penetration depth for a typical clinical treatment dose in pencil beam scanning mode.

Based on profile 10 obtained with the geometry according to the disclosure, the number of correlated counts for 1E8 protons is 27, clearly exceeding the uncertainty (about 13) on the number of uncorrelated counts at the position of the peak 11. It follows therefore that despite the fact that the spatial resolution of the profile obtained with the geometry of the disclosure is lower than for the prior art geometry, the geometry of the disclosure leads to better statistics (due to the larger slit width and less deep collimators), compared to the known design. For pencil beams applicable in practical clinical circumstances in terms of the number of protons per spot, this means that the simulated geometry 1 according to the disclosure allows to detect the beam range whereas this is not the case for the prior art designs.

The lower spatial resolution makes it more difficult to locate the Bragg peak and dose falloff region with a high accuracy based on any single profile obtained with the apparatus of the disclosure. However, the profile is nevertheless suitable for detecting a shift of the profile with respect to a reference profile, with a high accuracy, e.g. of about 1 mm. When the reference is determined and known to correspond to a pre-defined location of the Bragg peak, the calculation of a shift of a measured profile with respect to the reference allows to measure and monitor the Bragg peak location with the accuracy of the shift operation. The determination of the profile shift may take place according to known algorithms, for example applied for the knife edge slit camera for prompt gamma detection, as described in the above-cited references. The determination of the shift may involve approximating the prompt gamma count profile by a curve-fitting procedure and determining the shift of the curve with respect to a reference approximated curve. This is described in some detail in WO2012104416 for example, where the profile is approximated by a 3 line segment curve, but other approximations are applicable as well. The actual steps of determining the shift is therefore not described here in detail, and it suffices to say that the processor included in the detection device of an apparatus of the disclosure is preferably configured to determine the shift of the profile with respect to a reference profile. The determination of the shift may involve various ways of pre-processing the profile in order to correct for non-uniformities in the profile shape or to attenuate the impact of statistical variations. The pre-processing may involve a curve-fitting procedure as referred to above, but also smoothing techniques or the like can be used or combined with curve-fitting, for obtaining the best possible profile shape. The shift is then determined on the pre-processed profile, by measuring the distance of the profile from the reference profile in the direction of the beam line. The reference profile may be pre-processed in a similar manner as the measured profile.

It is to be noted that the prompt gamma curve shown in FIG. 2 is not normalized, as is seen in FIG. 2. The curve shift may be determined on the basis of said non-normalized profile, i.e. the profile expressing the total number of counts (preferably expressed per hadron particle and per unit length), as a function of the position within the target along the beam line. This provides the advantage that besides the beam range as such, the photon count profile obtained with the camera of the embodiment also allows to estimate the actual deposited dose.

The determination of the shift of the profile with respect to a reference profile is one way of taking advantage of the higher statistics obtainable with the prompt gamma camera according to the embodiment, i.e. having s, D and f according to the preferred ranges disclosed in the present specification. Other ways of exploiting these high statistics may be possible, based on other ways of treating or analysing the curve 10 illustrated in FIG. 2. The embodiment is therefore related to the apparatus as such, characterized by said ranges, which are to be regarded as purposive selections from the broader ranges that formed the starting point in reference 1 for example. It is to be noted that reference 1 follows a very different logic when it comes to determining optimal values of s, D and f, leading to a collimator that is more 'closed' (lower s, higher f) and 'deep' (higher D) than the collimator according to the embodiment.

Profile 30 is included in the graphs of FIG. 2 in order to illustrate that the improved counting statistics obtained with a prompt gamma camera according to some embodiments is not due to the different energy window selection. In reference 1, particles between 4 and 10 MeV are selected. The better statistics obtained by changing from 4-10 MeV to 2-7 MeV is however not sufficient. It is the change in geometry that is responsible for the better statistics.

The inventors have defined the term FRP (Falloff Retrieval Precision) for quantifying the precision with which a shift between a measured profile of a given statistic and a reference profile can be estimated. In order to estimate the precision with which the beam range can be retrieved, we start with the assumption that the expected profile is well known. To get this profile, which we will call "reference profile", either a high-statistics measurement or a high-statistics Monte Carlo simulation is used. In clinical practice, this reference profile will have to be predicted by Monte Carlo simulation or analytical models. This type of profile typically consists of a discrete set of points, either corresponding to detector pixels, collimator slits, or measurement points during a scan. To be able to predict the expectation of counts at any one point, the profile is then fitted with a continuous function, the reference function. Next comes the generation of a "sample" profile. This is a profile that stands for what would actually be measured during irradiation. It corresponds to a given number of protons delivered. It can be generated either by subsampling data gathered for the reference profile or by applying Poisson statistics and a random generator to the reference profile to obtain the appropriate statistical noise.

The sample profile is then matched to the reference function by applying a shift along the beam axis. When repeated many times with many independently generated sample profiles, the distribution of the obtained shifts gives an idea of how precisely the camera is able to measure a shift. Specifically, this standard deviation of the distribution is defined as the FRP. It is a good measure for the precision of the method for determining the Bragg peak and falloff position by shifting the profile.

Figure 3:
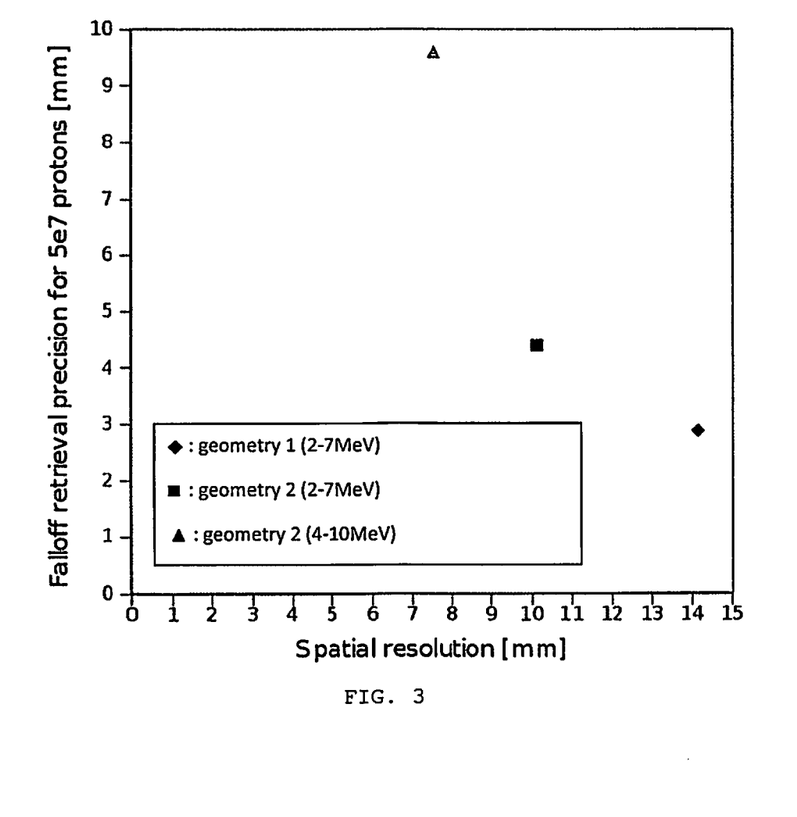
FIG. 3 illustrates the difference in terms of the Falloff Retrieval Precision and the spatial resolution of a prompt gamma profile, between a geometry according to the disclosure and according to known techniques.

FIG. 3 compares geometry 1 and 2 in terms of FRP value and spatial resolution, for a given number of protons. It can be seen that the geometry according to the some embodiments exhibits a worse spatial resolution, but a significantly better FRP value.

It is known in the art to apply a Time-of-Flight discrimination in the prompt gamma detection process, see for example document WO-A-2009141570. The TOF principle is based on a difference in the velocity between the prompt gamma photons travelling at the speed of light, and the slower background neutrons generated in the target. When a TOF discrimination is applied, the detection process in the prompt gamma camera is synchronised with the time structure of the proton beam. A proton beam generally has a pulsed character, the details of which depend on the type of accelerator used to produce the beam. For example, a cyclotron may typically produce a beam pulse every 10 ns with the width of the pulse being 1 ns. TOF prompt gamma detection applied in this case limits the prompt gamma measurement to a time window that is a fraction of the time delay between beam pulses, thereby diminishing the influence of neutron background emission. The smaller the TOF window, the more the neutron background is suppressed. As can be appreciated by the skilled reader, the TOF discrimination may be more complex for other time structures of a proton beam. In all cases however, the TOF discrimination has the effect of suppressing a percentage of the neutron background emission in the detected signal, and thus of conserving only a portion of that background emission.

The method according to the some embodiments is related to the use of a multi-slit prompt gamma camera for measurement of the prompt gamma profile in a target, irradiated by a pulsed hadron beam, wherein a TOF window may or may not (see further) be applied to the measurement. The degree to which the influence of background neutron emission is suppressed by the TOF discrimination has an influence on the optimal choice of the geometrical parameters s, D and f referred to above. The following parameter J is defined:

$$J = \frac{S \cdot A}{\sqrt{A_{TOF}}} \times 100 (\text{in } \%)$$

wherein:
S=spatial acceptance=1−f=s/(s+t)
A=angular acceptance=slit width/collimator depth (s/D)
$A_{TOF}$=TOF acceptance=ratio of neutron background emission that is conserved after application of the TOF discrimination, to the total neutron background emission. In the above-described case of the cyclotron producing a pulse at regular time intervals, this means that $A_{TOF}$=TOF window/delay between beam pulses.

In the example where the delay between pulses is 10 ns and the pulse width is 1 ns, this means that when the TOF window is 3 ns, $A_{TOF}$ is 0.3. According to the method of an embodiment, the value of J is higher than 1%, while the multi-slit camera dimensions s, D and f are defined as:
  s is 2 mm or higher
  D is between 50 mm and 200 mm
  f is lower than or equal to 0.7
The condition J>1% makes it possible to select values of s, D and f within these ranges such that the beam range can still be detected with an acceptable value of the FRP. According to 6 further embodiments, J is higher respectively than 1.5%, 2%, 2.5%, 3%, 3.5% or 4%.

According to a further embodiment of the method of an embodiment, the parameters s, D and f are defined as: s≤3 mm, D between 50 and 200 mm and f<0.5, i.e. as defined for the camera according to an embodiment. Further embodiments of the method of an embodiment are defined by the preferred sub-ranges for s, D and f as defined above in relation to the camera of an embodiment.

As stated, the parameter J and the condition J>1% is relevant to the use of a multi-slit camera in combination with a pulsed beam, wherein a form of TOF discrimination may be applied. The formula however includes the use of the camera without applying a TOF discrimination, which corresponds to $A_{TOF}$ being equal to 1. J can thus be calculated also for the above-described simulations based on geometries 1 and 2.

In the simulation based on geometry 2 wherein the slit width s, fill factor f and collimator depth D corresponded to the prior art camera described in reference 1 and wherein no TOF discrimination was applied, the parameter J equals 0.7%, i.e. lower than the value used in some embodiments. In order to meet the condition J>1%, a higher slit width s and/or a lower collimator depth D is used. In the simulation based on geometry 1 (according to the some embodiments, and also without TOF window) J equals 3.6%.

As explained above, while this may be counterintuitive, the comparison between the simulations of geometries 1 and 2 proves that a shift in the beam range can nevertheless be accurately determined, when values of D and s are applied which are very different from the optimized values of reference 1 (i.e. the opening width s is higher and the depth D of the collimator openings is lower). Even when J is higher than 2, 3 or 4, values of s and D are available for which an accurate range shift measurement can be done whilst not applying a TOF discrimination.

When a TOF discrimination is applied to the prompt gamma measurement, the condition J>1% favours the choice of lower values of s and/or higher values of D compared to the case where no TOF is applied. The application of the TOF window diminishes the effect of background radiation caused by neutron emission from the target. Hence the correlated signal to noise ratio increases and the slit width can be decreased in favour of a better spatial resolution, whilst the FRP remains acceptable. While neutron emission is suppressed by applying the TOF window, non-correlated photon emission is not, which favours the application of a thicker collimator (higher value of D) for eliminating these non-correlated photons by the higher shielding effect of such a thicker collimator. Again, because of the better signal to noise ratio, the FRP remains acceptable despite this higher value of D.

The reference to an 'acceptable' FRP means that any of the combinations of s, D and f defined in relation to the method of an embodiment (including values of s and D already applied in cameras known in the art), combined with a TOF window that allows the condition J>1% to be met, is capable of obtaining a number of correlated counts around the Bragg peak position that exceeds the statistical error on the number of uncorrelated counts per proton and per mm. While it is clear that for the lower values of s and the higher values of D and f within the ranges defined for the method of an embodiment, the application of a TOF discrimination is favoured, an embodiment also defines combinations of s, D and f with for example s lower than 3 mm, D higher than 150 mm and f higher than 0.5 that lead to J>1% without applying a TOF discrimination (i.e. with $A_{TOF}$=1).

As stated above, the multi-slit camera of some embodiments as such, i.e. defined by s≤3 mm, D between 50 mm and 200 mm and f<0.5, is a more 'open' camera than presently known in the art, i.e. a camera wherein the openings s are wider than the septa t. Especially when no TOF window is applied, the preferred ranges of the slit width s and collimator depth D are distinguished in an important way from the values that are presently applied in multi slit prompt gamma camera systems.

The inventors have further developed computer means and algorithms to compare a prompt gamma profile obtained with an optimized 'open' camera with a reference profile. With such an 'open' camera geometry, statistics of the prompt gamma is increased but the detection resolution is worse. Following the development of a preferred embodiment, it is demonstrated that by using such an open camera it is possible to determine shifts in penetration depth of the beam in the target with high accuracy. This is possible by introducing a reference profile and by comparing the reference profile with the measured prompt gamma profile.

The method of some embodiments defines a condition, in the form of J>1%, that makes it possible to detect the beam range with an acceptable FRP value within a broad range of multi-slit camera dimensions, including dimensions that are known in the art. The method of some embodiments preferably comprises the steps of determining a profile of prompt gamma count values as a function of the position along the beam line, and of determining the shift of the profile with respect to a reference profile, said steps as such being executable according to known methods, as for example described in WO2012104416, said steps being executed with a multi-slit camera as described in the present specification. More preferably, the method comprises the steps of:

acquiring a new profile of prompt gamma count values as a function of the position along the beam line, the prompt gammas being emitted from a target that is being irradiated by a hadron beam directed along a beam line, acquiring a reference profile, which may be a profile obtained from simulated data or from a previous measurement, optionally pre-processing the reference profile, optionally pre-processing the new profile, determining the shift of the new (optionally pre-processed) profile with respect to the (optionally pre-processed) reference profile, in the direction of the beam line.

The pre-processing may include curve-fitting and/or curve smoothing techniques of any kind known in the art.

The invention claimed is:

1. An apparatus for charged hadron therapy verification by detecting prompt gammas produced when irradiating a target with a charged hadron beam, the beam being directed along a beam line, the apparatus comprising:

a collimator comprising a plurality of collimator slabs of thickness (t), the collimator slabs being spaced apart to form an array of slit-shaped openings and configured to be placed at a right angle to the beam line to allow the passage of prompt gamma emission from the target, the collimator being defined at least by three geometrical parameters being:

the width (s) of the slit-shaped openings;

the depth (D) of the slit-shaped openings; and the fill factor (f), with f equal to t/(t+s); and a detection device configured for detecting the prompt gamma emission, the detection device comprising at least a portion of scintillator material aligned with each of the slit-shaped openings;

wherein the width s, the depth D, and the fill factor f are chosen such that:

s is 3 mm or higher;

D is between 50 mm and 200 mm; and f is lower than 0.5.

2. The apparatus according to claim 1, wherein D is between 50 mm and 100 mm.

3. The apparatus according to claim 2, wherein s is between 3 mm and 12 mm.

4. The apparatus according to claim 3, wherein s is higher than 4 mm.

5. The apparatus according to claim 4, wherein f is at least 0.25.

6. The apparatus according to claim 5, wherein the pitch p, with p=t+s, of the array of openings is equal to 5 mm or higher.

7. The apparatus according to claim 6, wherein the pitch p is between 5 mm and 20 mm.

8. The apparatus according to claim 7, wherein the openings as well as the slabs have mutually parallel sidewalls.

9. The apparatus according to claim 8, wherein the detection device is configured to determine a profile of prompt gamma count values as a function of the position along the beam line, and wherein the apparatus comprises a means for determining a shift of the profile with respect to a reference profile, in the direction of the beam line.

10. The apparatus according to claim 9, wherein the reference prompt gamma profile is obtained through at least one of a Monte Carlo simulation, an analytical model calculation or a previous measurement.

11. The apparatus according to claim 9, wherein the detection device comprises:

detectors in connection with the portions of scintillating material, the detectors producing a signal related to the number of photon counts registered in the portions of scintillating material; and a processor for receiving and processing the signals to determine the profile, wherein the processor is further configured to:

receive a reference profile, and determine the shift, in the direction of the beam line, of the profile with respect to the reference profile.

12. The apparatus according to claim 8, wherein the detection device is configured to determine a profile of prompt gammas detected through the slit-shaped openings and wherein the apparatus comprises computer means configured for comparing the profile of prompt gammas with a reference profile so as to determine a shift of a penetration depth of the hadron beam.

13. Apparatus according to claim 1, wherein the collimator material is tungsten.

14. The apparatus according to claim 1, wherein the detection device comprises an array of slabs of scintillator material, at least a portion of each slab being aligned with the slit-shaped openings.

15. A method for charged hadron therapy verification by detecting prompt gammas produced when irradiating a target with a charged hadron beam, the beam being directed along a beam line, wherein the prompt gammas are detected with an apparatus comprising:

a collimator comprising a plurality of collimator slabs of thickness (t), the collimator slabs being spaced apart to form an array of slit-shaped openings and placed at an essentially right angle to the beam line to allow the passage of prompt gamma emission from the target, the collimator being defined at least by three geometrical parameters being:

the width (s) of the slit-shaped openings;

the depth (D) of the slit-shaped openings; and the fill factor (f), with f equal to t/(t+s); and a detection device configured for detecting the prompt gammas emission, the detection device comprising at least a portion of scintillator material aligned with each of the slit-shaped openings;

wherein the width s of the openings, the depth D of the openings and the fill factor f are chosen such that:

s is 2 mm or higher;

D is between 50 mm and 200 mm;
f is lower than or equal to 0.7; and
a Time of Flight (TOF) discrimination is applied to the detection of the prompt gammas, and wherein J>1%, with J defined as $$\frac{S \cdot A}{\sqrt{A_{TOF}}}$$

and wherein:
S=spatial acceptance=1−f=s/(s+t);
A=angular acceptance=slit width/collimator depth (s/D); and
$A_{TOF}$=TOF acceptance=the ratio of neutron background emission that is conserved after application of the TOF discrimination, to the total neutron background emission, with $A_{TOF}$=1 when no TOF discrimination is applied.

16. The method according to claim 15, wherein s is 3 mm or higher and f is lower than 0.5.

17. The method according to claim 16, wherein a TOF discrimination is applied, wherein ATOF is lower than 1.

18. The method according to claim 17, wherein the target is a water phantom.

19. The method according to claim 18, further comprising the steps of:
determining a profile of prompt gamma count values as a function of the position along the beam line; and
determining the shift of the profile with respect to a reference profile.

20. The method according to claim 19, wherein the method further comprises the steps of:
acquiring a new profile of prompt gamma count values as a function of the position along the beam line, the prompt gammas being emitted from a target that is being irradiated by a hadron beam directed along a beam line;
acquiring a reference profile from simulated data or from a previous measurement; and
determining the shift of new profile with respect to the reference profile, in the direction of the beam line.

* * * * *